United States Patent
Cromwell (10) Patent No.: US 11,801,030 B2
(45) Date of Patent: *Oct. 31, 2023

(54) SYSTEMS AND METHODS FOR PREDICTING GASTROINTESTINAL IMPAIRMENT

(71) Applicant: University of Tennessee Research Foundation, Knoxville, TN (US)

(72) Inventor: John W. Cromwell, Iowa City, IA (US)

(73) Assignee: UNIVERSITY OF TENNESSEE RESEARCH FOUNDATION, Knoxville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/835,187

(22) Filed: Mar. 30, 2020

(65) Prior Publication Data

US 2020/0390415 A1    Dec. 17, 2020

Related U.S. Application Data (63) Continuation of application No. 14/876,930, filed on Oct. 7, 2015, now Pat. No. 10,603,006, which is a (Continued)

(51) Int. Cl.
*A61B 7/00* (2006.01)
*A61B 5/00* (2006.01)
(Continued)

(52) U.S. Cl.
CPC ............ *A61B 7/008* (2013.01); *A61B 5/4255* (2013.01); *A61B 5/6823* (2013.01);
(Continued)

(58) Field of Classification Search
CPC ... A61B 5/4255; A61B 5/6823; A61B 5/7275; A61B 2560/0456; A61B 7/008; G16H 50/30; G16H 50/70; G16H 50/20
See application file for complete search history.

(56) References Cited

U.S. PATENT DOCUMENTS

| | | | |
|---|---|---|---|
| 5,140,994 A | 8/1992 | Campbell et al. | |
| 5,301,679 A * | 4/1994 | Taylor .................... | A61B 7/008 600/528 |

(Continued)

FOREIGN PATENT DOCUMENTS

| | | |
|---|---|---|
| CN | 101541372 | 9/2009 |
| EP | 1956982 | 1/2015 |

(Continued)

OTHER PUBLICATIONS

International Search Report and Written Opinion dated Jul. 27, 2020 in International Patent Application No. PCT/US20/28600.

(Continued)

*Primary Examiner* — Patrick Fernandes
(74) *Attorney, Agent, or Firm* — ARNALL GOLDEN GREGORY LLP (57) ABSTRACT

Predicting gastrointestinal impairment may involve obtaining intestinal sounds of a patient to generate audio data, identifying predefined spectral events in the audio data that are predictive of subsequent gastrointestinal impairment, the spectral events being defined by predefined parameters, and predicting the likelihood of subsequent gastrointestinal impairment relative to the identified spectral events.

19 Claims, 6 Drawing Sheets

Related U.S. Application Data continuation of application No. 13/641,526, filed as application No. PCT/US2011/032616 on Apr. 15, 2011, now Pat. No. 9,179,887.

(60) Provisional application No. 61/324,879, filed on Apr. 16, 2010.

(51) Int. Cl.
  G16H 50/70 (2018.01)
  G16H 50/20 (2018.01)
  G16H 50/30 (2018.01)

(52) U.S. Cl.
  CPC .......... *A61B 5/7275* (2013.01); *G16H 50/20* (2018.01); *G16H 50/30* (2018.01); *G16H 50/70* (2018.01); *A61B 2560/0456* (2013.01)

(56) References Cited

U.S. PATENT DOCUMENTS

| | | | |
|---|---|---|---|
| 5,853,005 | A | 12/1998 | Scanlon |
| 6,056,703 | A | 5/2000 | Sandler et al. |
| 6,228,040 | B1 | 5/2001 | Craine |
| 6,287,266 | B1 | 9/2001 | Sandler et al. |
| 6,425,874 | B1 | 7/2002 | Sandler et al. |
| 6,520,924 | B2 | 2/2003 | Lee |
| 6,572,560 | B1 | 6/2003 | Watrous et al. |
| 6,629,937 | B2 | 10/2003 | Watrous |
| 6,776,766 | B2 | 8/2004 | Sandler et al. |
| 6,840,913 | B2 | 1/2005 | Mansy et al. |
| 8,715,201 | B2 | 5/2014 | Koehler et al. |
| 9,179,887 | B2 | 11/2015 | Cromwell |
| 10,603,006 | B2 | 3/2020 | Cromwell |
| 2002/0052559 | A1 | 5/2002 | Watrous |
| 2002/0058889 | A1 | 5/2002 | Lee |
| 2002/0156398 | A1 | 10/2002 | Mansy et al. |
| 2004/0032957 | A1 | 2/2004 | Mansy et al. |
| 2006/0025650 | A1* | 2/2006 | Gavriely ............... A61B 1/126 600/110 |
| 2007/0282174 | A1 | 12/2007 | Sabatino |
| 2008/0306355 | A1 | 12/2008 | Walker |
| 2010/0172839 | A1 | 7/2010 | Walker |
| 2013/0035610 | A1 | 2/2013 | Cromwell |
| 2013/0131532 | A1 | 5/2013 | Umana |
| 2015/0073306 | A1 | 3/2015 | Abeyratne et al. |
| 2015/0119758 | A1 | 4/2015 | Rogers et al. |
| 2016/0367823 | A1 | 12/2016 | Cowan et al. |
| 2017/0050006 | A1 | 2/2017 | Imran et al. |
| 2017/0340306 | A1 | 11/2017 | Spiegel et al. |
| 2018/0078195 | A1 | 3/2018 | Sutaria et al. |
| 2018/0303413 | A1 | 10/2018 | Hassan et al. |
| 2020/0330066 | A1 | 10/2020 | Cromwell |
| 2021/0000442 | A1 | 1/2021 | Marshall et al. |

FOREIGN PATENT DOCUMENTS

| | | |
|---|---|---|
| WO | WO-97/36543 | 10/1997 |
| WO | WO-2007/107908 | 9/2007 |
| WO | WO-2008/063938 | 5/2008 |
| WO | WO-2011/049293 | 4/2011 |
| WO | WO-2011/130589 | 10/2011 |
| WO | WO-2012/057406 | 5/2012 |
| WO | WO-2012/162740 | 12/2012 |
| WO | WO-2014/039404 | 3/2014 |
| WO | WO-2018/011631 | 1/2018 |
| WO | WO-2019/241674 | 12/2019 |

OTHER PUBLICATIONS

Chinese Search Report and English Language translation issued in related application No. CN 201180024426.5, dated Apr. 21, 2014.

Dalle et al., "Computer analysis of bowel sounds," Computers in Biology and Medicine, 1974; 4, pp. 257-256.

European Search Report issued in related application No. EP 11769638.5, dated Jul. 18, 2014.

First Examination Report issued by the Intellectual Property Office in India for related Indian Application No. 9563/CHENP/2012, dated Jul. 19, 2019.

Garner et al., "Non-invasive Topographic Analysis of Intestinal Activity in Man on the Basis of Acustic Phenomena," Res Exp Med., 1989; 189; pp. 129-140.

Sugrue et al., "Computerized Phonoenterography: The Clinical Investigation of a New System," Journal of Clinical Gastroenterology, 1994; 18(2): pp. 139-144.

Tomomasa et al., "Analysis of Gastrointestinal Sounds in Infants With Pyloric Stenosis Before and After Pyloromyotomy," [online], Pediatrics, 1999:104(5),pp. 1-4. Retrieved from the Internet: < URL: http://www.pediatrics.org/cgi/content/full/104/5/e60>, provided by University of Iowa Hospitals on Jan. 1, 2010.

Tomomasa et al., "Gastrointestinal Sounds and Migrating Motor Complex in Fasted Humans," The American Journal of Gastroenterology, 1999; 94(2), pp. 374-381.

Watson et al., "Phonoenterography: the recording and analysis of bowel sounds," Gut, 1967; 8(88), pp. 88-94.

Yong et al., "The study of Intestinal Sound Analyzer," Journal of Electronic Measurement and Instrument, 1995; 9(1), with English language translation, translated by Morningside Translations on Nov. 3, 2014, 14 pages total.

International Search Report and Written Opinion issued in PCT/US2021/036037, dated Sep. 9, 2021.

\* cited by examiner

SYSTEMS AND METHODS FOR PREDICTING GASTROINTESTINAL IMPAIRMENT

CROSS-REFERENCE TO RELATED APPLICATION

This application is a continuation of U.S. patent application Ser. No. 14/876,930 filed Oct. 7, 2015, granted as U.S. Pat. No. 10,603,006, which is a continuation of U.S. patent application Ser. No. 13/641,526, filed Oct. 16, 2012, granted as U.S. Pat. No. 9,179,887, which is a National Phase entry of International Patent Application No. PCT/US11/32616, filed Apr. 15, 2011, which claims benefit of U.S. Provisional Application No. 61/324,879, filed Apr. 16, 2010, the contents of each are incorporated by reference herein in their entirety.

BACKGROUND

Gastrointestinal impairment (GII) is common following surgical procedures. Such impairment is often the result of postoperative ileus, a condition in which a portion of the intestines is temporarily paralyzed and therefore cannot process food. Although GII most often occurs after an abdominal surgery, it is not uncommon for GII to occur after other types of surgery. In addition to interfering with postoperative oral feeding, GII can cause abdominal distension, nausea, emesis, and pulmonary aspiration.

Concern over GII often results in the implementation of various postoperative care protocols that prolong hospitalization, even though the majority of patients will not experience GII. Such protocols often include the use nasogastric tubes, motility agents, and hyperalimentation. In addition to causing patient discomfort and inconvenience, those protocols and extended hospital stays add to the expense of postoperative care. Indeed, it is currently estimated that postoperative GII add $2.7 billion in costs to U.S. health care.

It is an understandable goal of the health care industry to determine which patients are at risk of GII prior to beginning oral re-feeding after surgery because early intervention or alteration of the re-feeding regimen may enable avoidance of the consequences of GII and could reduce costs. Unfortunately, no reliable method for determining which patients are physiologically at risk for GII in the early postoperative period is currently available.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, gastrointestinal impairment (GII) is common following surgical procedures. Unfortunately, no reliable method for determining which patients are at risk for GII is currently available. Disclosed herein are systems and methods for predicting GII based upon the patient's intestinal sounds. As is described below, the disclosed systems and methods identify discrete acoustic spectral events within the intestinal sounds, which can be used to predict subsequent GII. Those spectral events are good indicators of intestinal tract function because the sounds are produced by motor activity within the bowel.

In the following disclosure, various embodiments are described. It is to be understood that those embodiments are mere example implementations of the inventions and that other embodiments are possible. All such other embodiments are intended to fall within the scope of this disclosure.

Figure 1:
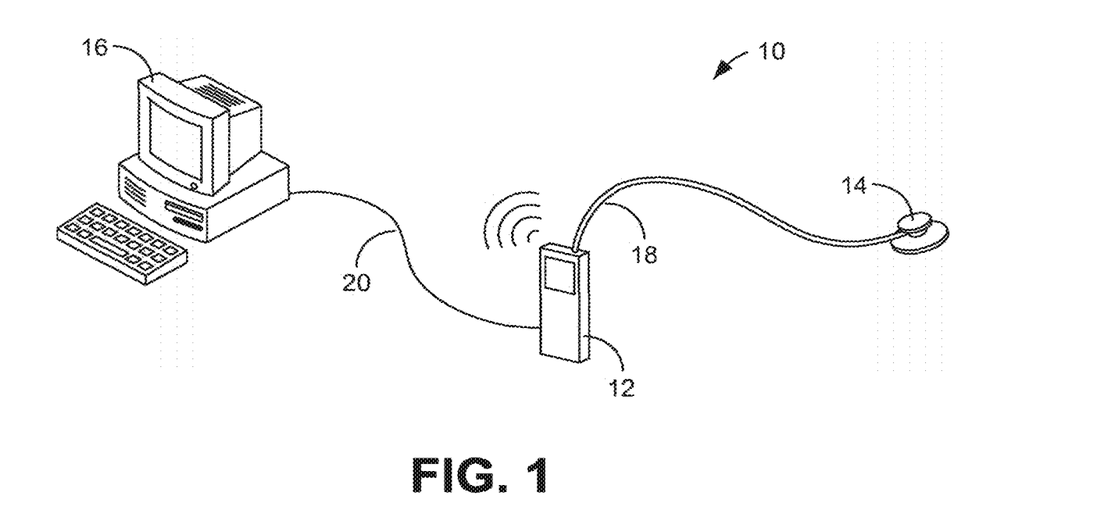
FIG. 1 is a schematic diagram that illustrates a first embodiment of a system for predicting gastrointestinal impairment

FIG. 1 illustrates a first example system 10 for predicting gastrointestinal impairment. As is indicated in FIG. 1, the system 10 generally comprises a data collection device 12, a patient interface 14, and a computer 16. The data collection device 12 can comprise any device that is capable of collecting audio data that is generated within a patient's intestinal tract. In some embodiments, the data collection device 12 comprises a portable (e.g., handheld) digital audio recorder. In such a case, the data collection device 12 can comprise an integral microphone (not shown) that is used to capture the intestinal sounds.

The patient interface 14 is a device that can be directly applied to the patient's abdomen for the purpose of picking up intestinal sounds. In some embodiments, the patient interface 14 comprises, or is similar in design and function to, a stethoscope head. Stethoscope heads comprise a diaphragm that is placed in contact with the patient and that vibrates in response sounds generated within the body. Those sounds can be delivered to the microphone of the data collection device 12 via tubing 18 that extends between the patient interface 14 and the data collection device. Specifically, acoustic pressure waves created from the diaphragm vibrations travel within an inner lumen of the tubing 18 to the microphone. In some embodiments, all or part of the patient interface 14 is disposable to avoid cross-contamination between patients. Alternatively, the patient interface 14 can be used with a disposable sheath or cover (not shown) that can be discarded after use.

The audio data collected by the data collection device 12 can be stored within internal memory of the device. For example, the audio data can be stored within nonvolatile memory (e.g., flash memory) of the device 12. That data can then be transmitted to the computer 16 for processing. In some embodiments, the data is transmitted via a wire or cable 20 that is used to physically connect the data collection device 12 to the computer 16. In other embodiments, the data can be wirelessly transmitted from the data collection device 12 to the computer 16 using a suitable wireless protocol such as Bluetooth or Wi-Fi (IEEE 802.11).

The computer 16 can, in some embodiments, comprise a desktop computer. It is noted, however, that substantially any computing device that is capable of receiving and processing the audio data collected by the data collection device 12 can be used. Therefore, the computer 16 can, alternatively, take the form of a mobile computer, such as a notebook computer, a tablet computer, or a handheld computer. It is further noted that, although the data collection device 12 and the computer 16 are illustrated in FIG. 1 as comprising separate devices, they can instead be integrated into a single device, for example a portable (e.g., handheld) computing device. For example, the data collection device 12 can be provided with a digital signal processor and appropriate software/firmware that can be used to analyze the collected audio data.

Figure 2:
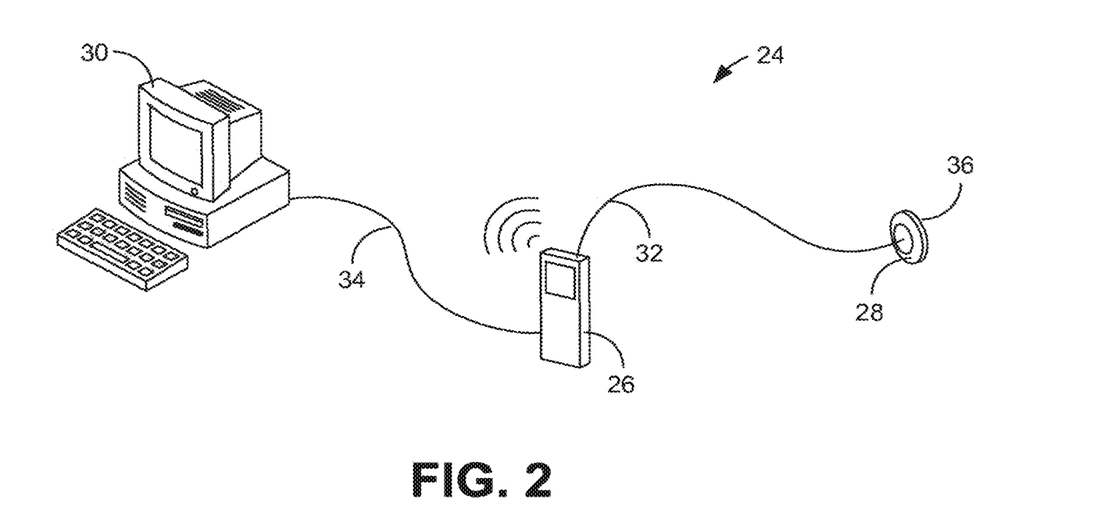
FIG. 2 is a schematic diagram that illustrates a second embodiment of a system for predicting gastrointestinal impairment.

FIG. 2 illustrates a second example system 24 for predicting gastrointestinal impairment. As indicated in FIG. 2, the system 24 shares several similarities with the system 10 illustrated in FIG. 1. Therefore, the system 24 generally comprises a data collection device 26, a patient interface 28, and a computer 30. In the system 24 of FIG. 2, however, the patient interface 28 comprises a device having its own integral microphone (not shown). In such a case, patient sounds are picked up by the microphone of the patient interface 28 and are converted into electrical signals that are electronically transmitted along a wire or cable 32 to the data collection device 26 for storage and/or processing. Alternatively, the patient sounds can be transmitted to the data collection device 26 wirelessly. In some embodiments, the patient interface 28 has an adhesive surface 36 that enables the interface to be temporarily adhered to the patient's skin in similar manner to an electrocardiogram (EKG) lead. As with the previous embodiment, patient data can be transmitted from the data collection device 26 to the computer 30 via a wired connection (via wire or cable 34) or wirelessly.

Figure 3:
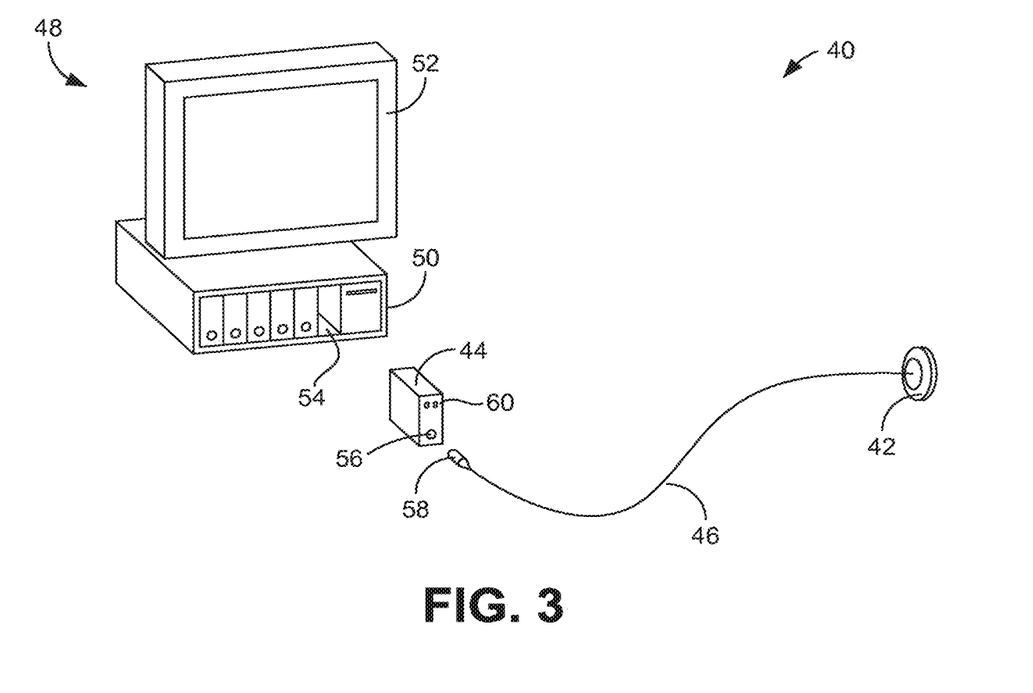
FIG. 3 is a schematic diagram that illustrates a third embodiment of a system for predicting gastrointestinal impairment.

FIG. 3 illustrates a third example system 40 for predicting gastrointestinal impairment. The system 40 comprises a patient interface 42 and a data collection device 44. As with the system 24 of FIG. 2, the patient interface 42 can comprise a device having its own integral microphone (not shown) and patient sounds picked up by the microphone can be electronically transmitted along a wire or cable 46 to the data collection device 44. In the embodiment of FIG. 3, however, the data collection device 44 comprises a component that is designed to dock with a patient monitoring system 48, which may be located beside the patient's bed. Such patient monitoring systems 48 are currently used to monitor other patient parameters, such as blood pressure and oxygen saturation. In the example of FIG. 3, the patient monitoring system 48 comprises a docking station 50 and an associated display 52. In such a case, the data collection device 44 can dock within a free bay 54 of the station prior to use.

In some embodiments, the data collection device 44 comprises no internal power supply and therefore can only collect patient data when docked. By way of example, the data collection device 44 can have electrical pins (not shown) that electrically couple the device to the patient monitoring system 48 for purposes of receiving power and transferring collected data to the patient monitoring system. The patient data can then be stored in memory of the patient monitoring system 48 and/or can be transmitted to a central computer for storage in association with a patient record in an associated medical records database.

As is further shown in FIG. 3, the data collection device 44 comprises an electrical port 56 that can receive a plug 58 of the wire or cable 46. In addition, the data collection device 44 can comprise one or more indicators 60, such as light-emitting diode (LED) indicators that convey information to the operator, such as positive electrical connection with the patient monitoring system 48 and patient signal quality.

Figure 4:
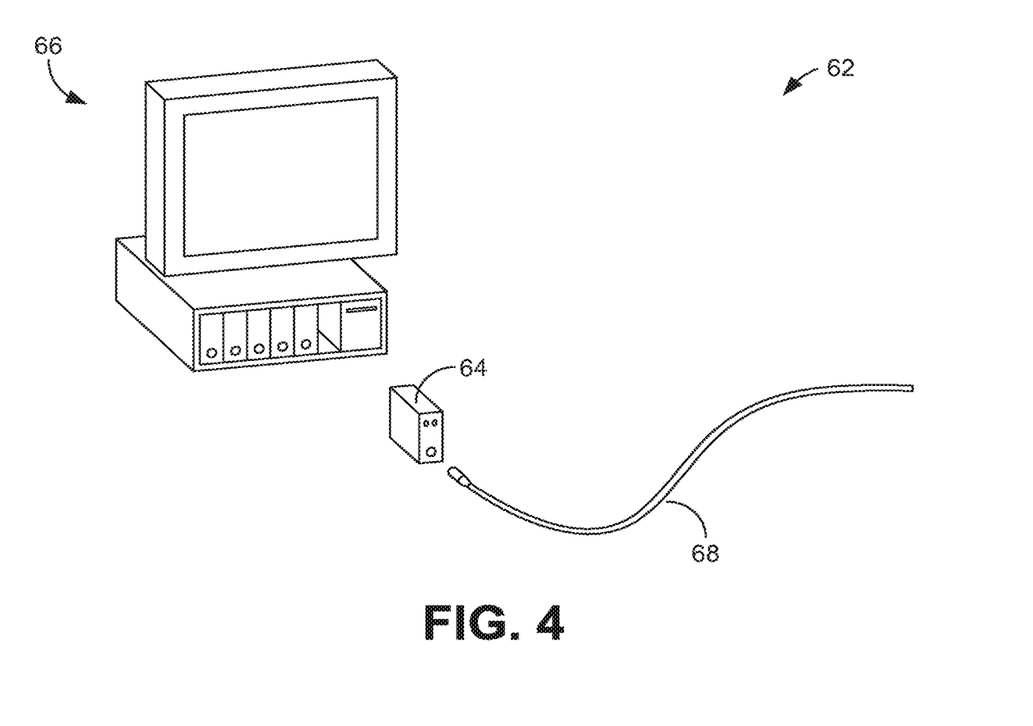
FIG. 4 is a schematic diagram that illustrates a fourth embodiment of a system for predicting gastrointestinal impairment.

FIG. 4 illustrates a fourth example system 62 for predicting gastrointestinal impairment. Like the system 40 of FIG. 3, the system 62 comprises a data collection device 64 that couples with a patient monitoring system 66. However, instead of an external patient interface, the system 62 comprises an internal patient interface 68 that is designed to collect sounds from within the peritoneal cavity. By way of example, the patient interface 68 comprises a small diameter microphone catheter that is left in place after surgery has been completed, in similar manner to a drainage catheter. Such a patient interface may be particularly useful in cases in which the patient is obese and it is more difficult to obtain high-quality signals from the surface of the skin. To avoid passing current into the patient, the patient interface 68 can comprise a laser microphone. In such a case, a laser beam is directed through the catheter and reflects off a target within the body. The reflected light signal is received by a receiver that converts the light signal to an audio signal. Minute differences in the distance traveled by the light as it reflects from the target are detected interferometrically. In alternative embodiments, the patient interface 68 can comprise a microphone that is positioned at the tip of the catheter.

As described above, FIGS. 1-4 illustrate four different example embodiments of a system for predicting gastrointestinal impairment. It is noted that combinations of those systems are possible. For instance, the user interface 68 shown in FIG. 4 could be used with the data collection device 12 of FIG. 1, if desired. All such combinations are considered to be within the scope of this disclosure.

Figure 5:
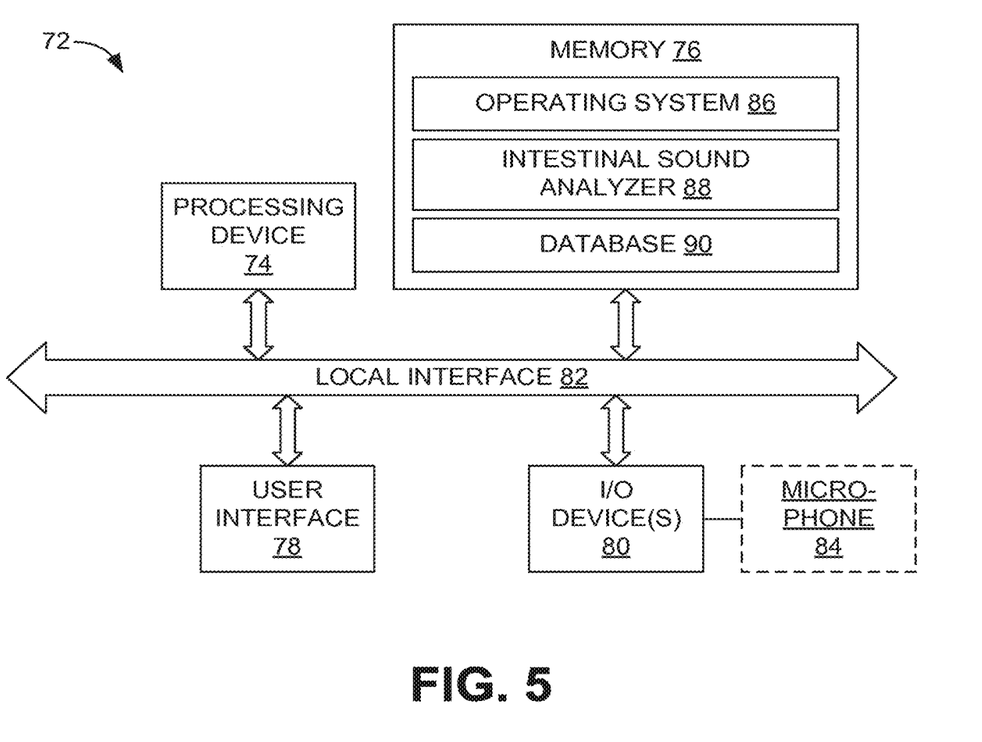
FIG. 5 is a block diagram of an embodiment of the architecture of a device, such as one of those shown in FIGS. 1-4, that can process collected patient data to assist in the gastrointestinal impairment predication.

FIG. 5 illustrates an example architecture for a device 72 that can be used in a system for predicting gastrointestinal impairment to analyze collected patient data. By way of example, the architecture shown in FIG. 5 can be the architecture of the computer 16 or 30 shown in FIGS. 1 and 2 respectively, the data collection device 12, 26, 44, or 64 shown in FIGS. 1, 2, 3, and 4 respectively, or the patient monitoring system 48 or 66 shown in FIGS. 3 and 4 respectively. Moreover, it is noted that the illustrated architecture can be distributed across one or more devices.

As is indicated in FIG. 5, the device 72 generally comprises a processing device 74, memory 76, a user interface 78, and input/output devices 80, each of which is coupled to a local interface 82, such as a local bus.

The processing device 74 can include a central processing unit (CPU) or other processing device, such as a microprocessor or digital signal processor. The memory 76 includes any one of or a combination of volatile memory elements (e.g., RAM) and nonvolatile memory elements (e.g., flash, hard disk, ROM).

The user interface 78 comprises the components with which a user interacts with the device 72. The user interface 78 can comprise, for example, a keyboard, mouse, and a display device, such as a liquid crystal display (LCD). Alternatively or in addition, the user interface 78 can comprise one or more buttons and/or a touch screen. The one or more I/O devices 80 are adapted to facilitate communication with other devices and may include one or more electrical connectors and a wireless transmitter and/or receiver. In addition, in cases in which the device 72 is the data collection device, the I/O devices 80 can comprise a microphone 84.

The memory 76 is a computer-readable medium and stores various programs (i.e., logic), including an operating system 86 and an intestinal sound analyzer 88. The operating system 86 controls the execution of other programs and provides scheduling, input-output control, file and data management, memory management, and communication control and related services. The intestinal sound analyzer 88 comprises one or more algorithms that are configured to analyze intestinal audio data for the purpose of predicting the likelihood of a patient developing GII. In some embodiments, the analyzer 88 conducts that analysis relative to correlation data stored in a database 90 and presents to the user (e.g., physician or hospital staff) a predictive index of GII risk. In some embodiments, the analyzer 88 identifies particular spectral events of interest using target signal parameters, signal-to-noise ratio parameters, and noise power estimation parameters. Decision tree analysis of the number of predictive spectral events during a specified time interval can then be used to communicate a high-, intermediate-, or low-risk of GII. In some embodiments, the risk associated with each level of risk is 83%, 30%, and 0%, respectively.

Figure 6:
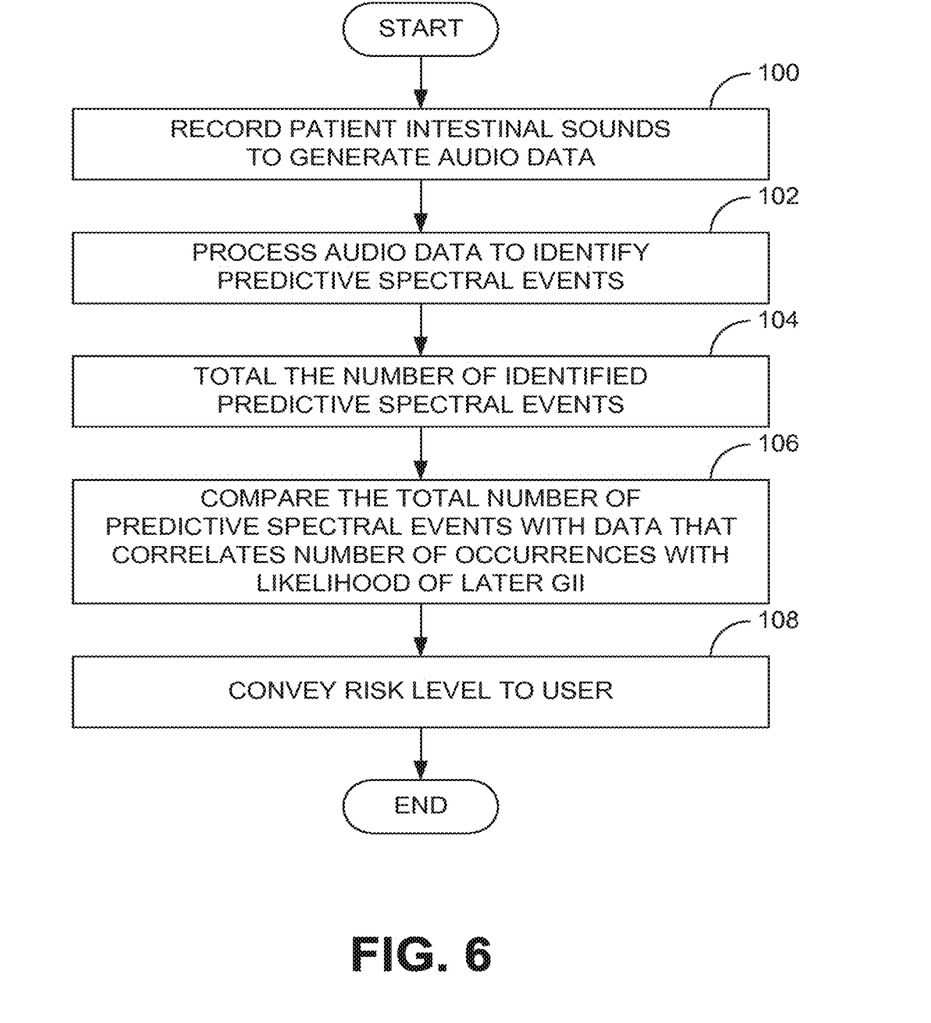
FIG. 6 is a flow diagram of an embodiment of a method for predicting gastrointestinal impairment.

FIG. 6 illustrates an embodiment of a method for predicting GII. Beginning with block 100, patient intestinal sounds are recorded to generate an audio data. As described above, the sounds can be obtained non-invasively, for example using a stethoscope head or other patient interface that is applied to the patient's skin on or near the abdomen. Alternatively, the sounds can be collected with a device that extends into the patient's peritoneal cavity. The sounds can be recorded early in the postoperative period, for example the day of or a day immediately following surgery. Regardless of when the sounds are recorded, they are recorded for a duration of time that is sufficient to enable identification of spectral events that are predictive of intestinal function. By way of example, sounds are recorded for a period of approximately 4 to 6 minutes. In some embodiments, all sounds within the 20-20,000 Hz range are recorded. Filters can be applied, however, to reduce the range of frequencies that are recorded, and therefore reduce the amount of data that is analyzed. In some embodiments, filters are used so that only sounds with frequencies from approximately 700 to 1500 Hz are recorded or analyzed. Although the sounds have been described as being "recorded," it will be understood that the sounds can alternatively simply be obtained and real-time processed (as described below) without actually recording the sounds.

Once the audio data is generated, the data is processed, for example in real time, to identify one or more predictive spectral signals, as indicated in block 102. As described above, the sounds that are generated by the intestines are the result of peristalsis. The sounds therefore provide an indication of how the bowels are functioning. For example, paralysis of significant portions of the intestinal tract will proportionally reduce the number of high-energy propulsive contractions in the gut, which results in the loss of some of the higher energy, and thus higher frequency, acoustic spectrum that is typical with normally functioning bowels. As described below, it has been determined that certain predefined spectral events can be identified within the sounds that are highly predictive of whether GII is or is not likely to occur. As is also described below, each of the predefined spectral events is defined by particular characteristics or parameters, such as their frequency, amplitude, duration, and separation in time from other spectral events.

After the spectral events have been identified, their number during a specified duration of time (e.g., the total duration of the recording) are totaled, as indicated in block 104. At this point, the total number of spectral events is compared to correlation data that correlates the number of spectral events with the likelihood of later GII, as indicated in block 106. As an example, a spectral event designated as "MH4" was identified in a study described below. With MH4, a high risk of GII exists if the number of observed MH4 events is less than approximately 21 times during four minutes of recording, an intermediate risk of GII exists if the number of observed MH4 events is greater than approximately 21 but less than approximately 131 times during four minutes of recording, and a low risk of GII exists if the number of observed MH4 events is greater than approximately 131 times during four minutes of recording. The number of predefined spectral events therefore can be used as an index that conveys the magnitude of the risk for GII, with a lower number indicating greater risk and a higher number indicating lower risk.

Once the likelihood of later GII has been determined, that risk can be conveyed to the user, as indicated in block 108. For example, the computer or other device used to perform the analysis can display the risk level on an associated display. In some embodiments, the risk can be conveyed as an index (i.e., a number). In other embodiments, the risk can be indicated as being "high," "moderate," or "low." Regardless, appropriate action can then be taken relative to the indication and may comprise permitting or prohibiting oral feeding. Notably, further recordings and analysis can be performed on the patient in the ensuing days after surgery to evaluate bowel function and confirm the initial patient assessment.

As can be appreciated from the above-described method, the risk of GII can be assessed much in the same way that the risk of heart problems can be non-invasively assessed with an EKG. In some embodiments, the risk assessment can be performed real-time.

A clinical study was performed to evaluate the viability of the disclosed systems and methods. One goal of the study was to confirm that spectral events present in intestinal sounds early in postoperative period do in fact correlate with GII subsequently, before clinical signs and symptoms develop. Another goal of the study was to develop a model for predicting GII that can be implemented as a simple, noninvasive, point-of-care test that will enable hospitals and other institutions to risk stratify patients for development of clinically significant GII using analysis of intestinal sounds.

In the study, patients who were scheduled to undergo inpatient surgery were recruited using an IRB-approved protocol. Patients undergoing abdominal and non-abdominal surgeries were included. Those who were admitted to the ICU postoperatively were excluded from the remainder of the study.

A device for digitally recording abdominal sounds was assembled using a dual-channel digital audio recorder (Microtrak II, M-Audio Corp., Irwindale, Calif.), condenser microphone (ATR35s, Audio-Technica Ltd, Leeds, UK), stethoscope tubing, and stethoscope heads. For recording intestinal sounds, the stethoscope heads were applied to the upper and lower anterior abdominal wall and both channels were recorded simultaneously for a period of 5-6 minutes. A standardized tone was also applied to each recording to calibrate audio levels.

Recordings of intestinal sounds were performed by the research team immediately preoperatively and then on each postoperative day. The research team also collected clinical outcome data on a daily basis. Variables related to the development of GII are shown in Table 1. The clinical team providing patient care was blinded to the results of the audio recordings.

TABLE 1

Clinical variables collected daily related to presence of GII.

Diet Started
Diet Type
Hours since last meal
Abdominal Distension Present
Emesis
Flatus
Bowel movement
Reversal of diet
Motility agent prescribed
Toleration of diet for 24 h Audio recordings were subsequently processed using digital signal processing algorithms. The algorithms were applied in an iterative fashion focusing on identifying spectral events preoperatively or in the early postoperative period that would predict the development of GII during the remainder of the hospital stay. Five types of spectral events that span different portions of the audible spectrum were ultimately used for the analyses. Each type of spectral event was defined by unique target signal parameters (minimum and maximum frequency, minimum and maximum duration, and minimum separation), signal-to-noise ratio parameters (minimum occupancy, signal-to-noise threshold), and noise power estimation parameters (block size, hop size, percentile). The five spectral events were designated H4, M4, L4, ML4, and MH4, and the parameters for each are shown in Table 2. Spectral events were counted over a four-minute interval of time. GII was defined as the presence of emesis, the need for nasogastric intubation, or the reversal of the diet.

TABLE 2

Detector settings for the defined spectral events.

| Event Name | Target Signal Parameters | | | | | Signal-to-Noise Ratio Parameters | | Noise Power Estimation Parameters | | |
|---|---|---|---|---|---|---|---|---|---|---|
| | Min. Freq. (hz) | Max. Freq. (hz) | Min. Dur. (ms) | Max. Dur. (ms) | Min. Sep. (ms) | Min. Occupancy (%) | SNR Threshold (dB) | Block Size (ms) | Hop Size (ms) | Percentile (%) |
| L4 | 20 | 400 | 23 | 600 | 11.6 | 66 | 10.0 | 1004 | 499 | 15.0 |
| M4 | 400 | 1400 | 23 | 600 | 29 | 67 | 10.0 | 1497 | 499 | 20.0 |
| H4 | 1400 | 20000 | 5.8 | 600 | 20 | 70 | 10.0 | 1198 | 600 | 20.0 |
| ML4 | 400 | 900 | 5.8 | 600 | 20 | 70 | 10.0 | 1198 | 600 | 20.0 |
| MH4 | 900 | 20000 | 5.8 | 600 | 20 | 70 | 10.0 | 1198 | 600 | 20.0 |

RavenPro 1.4 software was used for visualization, analysis, and measurement of the recorded audio signals. Statistical analyses were performed using PASW 18 and Clementine 10.1.

Thirty-seven patients were recruited into the study. Five patients were excluded due to admission to the ICU postoperatively. Two patients discharged on the day of operation were excluded as no postoperative data was acquired. Of the remaining thirty patients, eleven were male and nineteen were female. The mean age was 52 (SD=12). Five patients had extra-abdominal operations and twenty-five patients had intra-abdominal operations. Nine patients (30% of the total) subsequently developed GII, all within the first four postoperative days. Of those patients, four began on POD1, one on POD2, and four on POD4.

Figure 7:
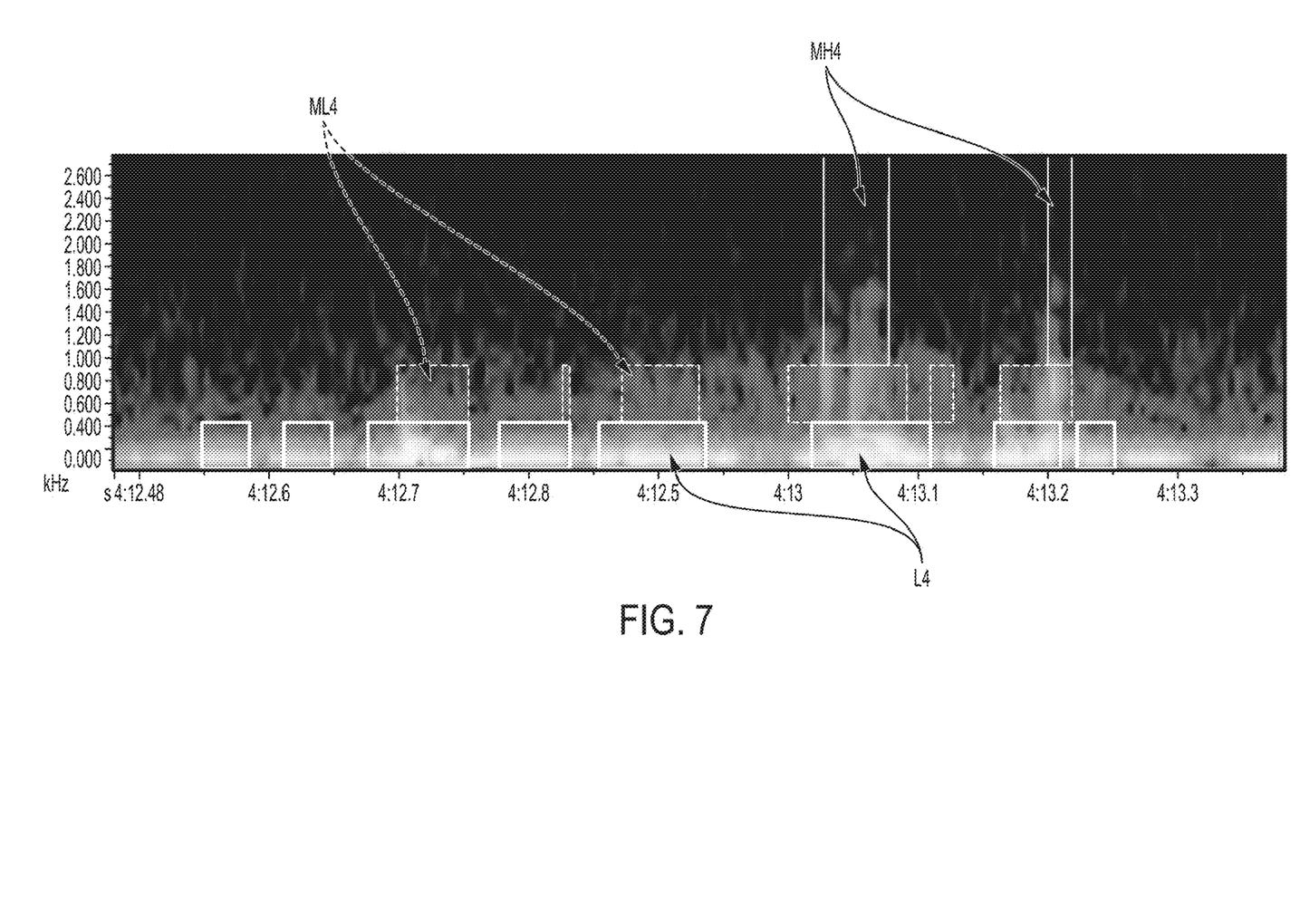
FIG. 7 is an example spectrogram illustrating spectral events contained in recorded abdominal sounds.

Examples of three of the spectral events are shown in a spectrogram of FIG. 7. The mean number of spectral events of each designation was calculated for patients who did or did not subsequently exhibit GII. A two-tailed t-test was then used to assess the significance of any differences. Spectral events obtained from POD0 did not correlate with subsequent development of GII (Table 3). Spectral events obtained from POD1, however, did prove to correlate with subsequent development of GII (Table 4). Specifically, MH4 spectral events had a mean count of 154 in patients without subsequent GII and 44 in those who did develop GII (p=0.004).

TABLE 3

Correlation of POD0 spectral events with development of GII.

POD0

| Spectral Event | Postop GII | N | Mean Count | 2-tailed t-test |
|---|---|---|---|---|
| L4 | No | 21 | 3357 | .55 |
| | Yes | 9 | 3247 | |
| M4 | No | 21 | 216 | 0.80 |
| | Yes | 9 | 232 | |
| H4 | No | 21 | 32 | .37 |
| | Yes | 9 | 45 | |
| ML4 | No | 21 | 919 | .84 |
| | Yes | 9 | 949 | |
| MH4 | No | 21 | 268 | .10 |
| | Yes | 9 | 398 | |

TABLE 4

Correlation of POD1 spectral events with development of GII.

POD1

| Spectral Event | Postop GII | N | Mean Count | 2-tailed t-test |
|---|---|---|---|---|
| L4 | No | 21 | 3690 | .62 |
| | Yes | 9 | 3620 | |
| M4 | No | 21 | 314 | .08 |
| | Yes | 9 | 218 | |

TABLE 4-continued

Correlation of POD1 spectral events with development of GII.
POD1

| Spectral Event | Postop GII | N | Mean Count | 2-tailed t-test |
|---|---|---|---|---|
| H4 | No | 21 | 30 | .09 |
|  | Yes | 9 | 9 |  |
| ML4 | No | 21 | 1234 | .51 |
|  | Yes | 9 | 1128 |  |
| MH4 | No | 21 | 154 | .004 |
|  | Yes | 9 | 44 |  |

CHAID decision-tree analysis was then applied to develop a predictive model using this data as a training data set. Using CHAID analysis, two cut-off values for MH4 (at 21 and 131) were determined as measured on POD1 that could stratify the data set into low risk, intermediate risk, and high risk for subsequent GII (Table 5).

TABLE 5

Risk strata proposed based upon POD1 measurements of MH4.

| Risk Strata | n | MH4 POD1 | Risk of Subsequent GII |
|---|---|---|---|
| Low Risk | 12 | >131 | 0% |
| Intermediate Risk | 12 | 21-131 | 30% |
| High Risk | 6 | <21 | 83% |

Figure 8:
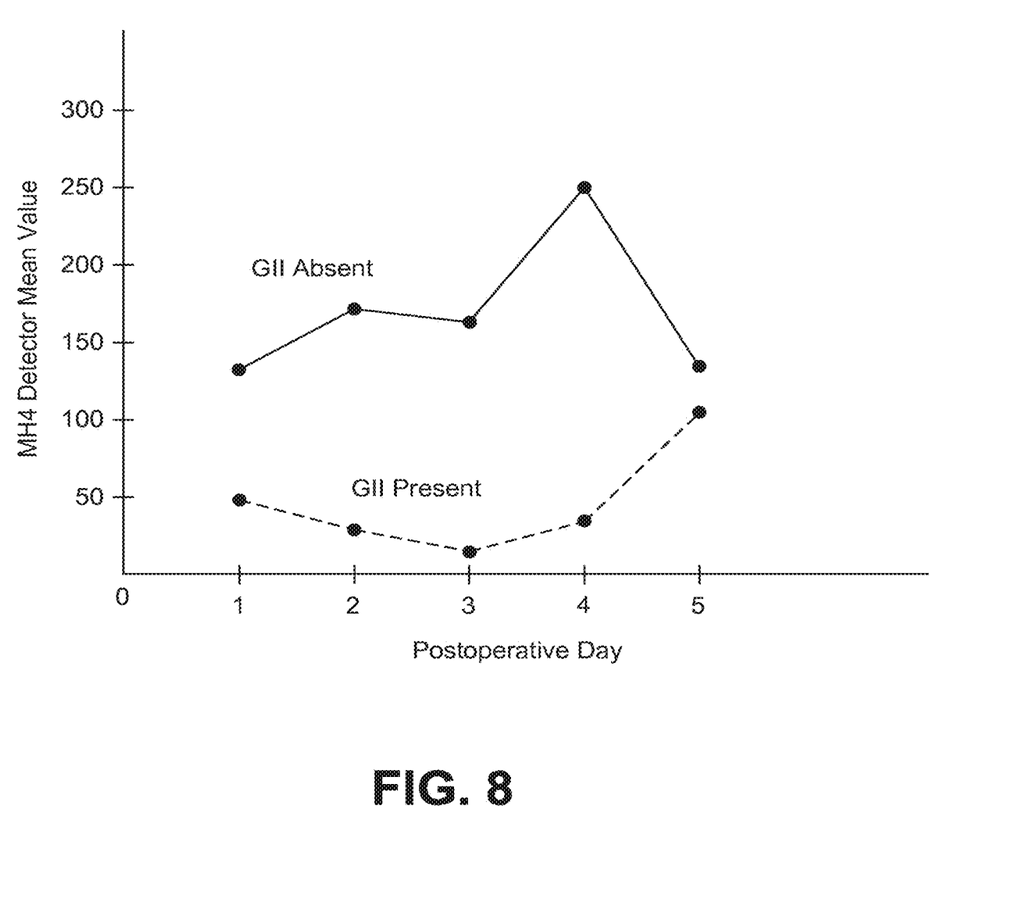
FIG. 8 is a graph that plots temporal changes in a particular spectral event (MH4) in patients with and without gastrointestinal impairment.

The mean temporal changes in MH4 were examined in patients with and without GII. FIG. 8 is a graph that plots temporal changes in MH4 spectral events.

The results of the study confirmed that spectral events present in intestinal sounds early in the surgical stay do in fact correlate with GII before clinical signs and symptoms develop. In particular, it was determined that MH4 segregated highly and significantly with the presence of subsequent GII. A predictive model based on MH4 measurement therefore can be used to evaluate patients as being of high-, intermediate-, and low-risk for GII. Significantly, no patients in the low-risk group developed GII. In the study, the predictive value of low-risk classification for no GII was 100%, while the predictive value of high-risk classification for GII was 83%. Thirty percent (30%) of the intermediate-risk patients experienced GII.

It is believed that powerful models can be generated from a larger data set of patients and by monitoring intestinal sounds during extended periods of time, such as a 24-hour period. Continuous recording with data averaging and adding additional types of spectral analysis may improve the predictive accuracy of the disclosed technique. Future trials are anticipated that will focus on gathering larger sets of data, validating the proposed predictive model, refining the spectral events analyzed, assessing alternate timings of data collection, and developing widely applicable predictive models. In addition, further development of reliable technology for rapid, point-of-care data continuous acquisition and analysis will be invaluable in expanding these investigations and ultimately in any clinical use. Regardless, the above-described study confirms the feasibility and promise of using acoustic spectral analysis in the study of GII and other gastrointestinal disorders.

The invention claimed is:

1. A method for predicting gastrointestinal impairment, the method comprising:
obtaining audio data from intestinal sounds of a patient with a patient interface;
wherein the patient interface comprises a single microphone, and the single microphone detects the intestinal sounds of the patient;
transmitting the audio data to a data collection device;
identifying, by a processor, predefined spectral events in the audio data that are predictive of subsequent gastrointestinal impairment, the predefined spectral events being defined by predefined parameters; and
predicting a likelihood of subsequent gastrointestinal impairment relative to the predefined spectral events.

2. The method of claim 1, wherein the patient interface is a non-invasive external device.

3. The method of claim 1, wherein the patient interface is positioned within the patient's peritoneal cavity.

4. The method of claim 1, wherein the predefined parameters include frequency of the predefined spectral events and the frequency is in the range of approximately 900 to 20,000 Hertz.

5. The method of claim 1, wherein the predefined parameters include duration of the predefined spectral events and the duration is in the range of approximately 5 to 600 milliseconds.

6. The method of claim 1, wherein the predefined parameters include minimum separation in time of the predefined spectral events from other spectral events and the minimum separation in time is approximately 20 milliseconds.

7. The method of claim 1, wherein the predefined parameters include signal-to-noise ratio of the predefined spectral events and the signal-to-noise ratio threshold is approximately 10 decibels.

8. A non-transitory computer-readable medium including program instructions that when executed by a processor cause the processor to perform the following actions:
identifying, by a processor, predefined spectral events in audio data obtained from intestinal sounds of a patient, the predefined spectral events being defined by predefined parameters and predictive of subsequent gastrointestinal impairment;
wherein the audio data is obtained by a patient interface and transmitted to a data collection device; wherein the patient interface comprises a single microphone, and the single microphone detects the intestinal sounds of the patient; and
predicting a likelihood of subsequent gastrointestinal impairment relative to the predefined spectral events, wherein predicting the likelihood of subsequent gastrointestinal impairment comprises counting the total number of spectral events that occurred in a predefined period of time and comparing the number to an index that gauges the risk of subsequent gastrointestinal impairment relative to the number of spectral events.

9. The non-transitory computer-readable medium of claim 8, wherein the predefined parameters include frequency of the predefined spectral events and the frequency is in the range of approximately 900 to 20,000 Hertz.

10. The non-transitory computer-readable medium of claim 8, wherein the predefined parameters include duration of the predefined spectral events and the duration is in the range of approximately 5 to 600 milliseconds.

11. The non-transitory computer-readable medium of claim 8, wherein the predefined parameters include minimum separation in time of the predefined spectral events from other spectral events and the minimum separation in time is approximately 20 milliseconds.

12. The non-transitory computer-readable medium of claim 8, wherein the predefined parameters include signal-to-noise ratio of the predefined spectral events and the signal-to-noise ratio threshold is approximately 10 decibels.

13. A system for predicting gastrointestinal impairment, the system comprising:
   a device to identify predefined spectral events in audio data obtained from intestinal sounds of a patient, the predefined spectral events being defined by predefined parameters and predictive of subsequent gastrointestinal impairment;
   wherein the audio data is obtained by a patient interface and transmitted to a data collection device;
   wherein the patient interface comprises a single microphone, and the single microphone detects the intestinal sounds of the patient; and
   the device further being configured to predict the likelihood of subsequent gastrointestinal impairment relative to the predefined spectral events, wherein the device predicts the likelihood of subsequent gastrointestinal impairment by counting a total number of spectral events that occurred in a predefined period of time and comparing the total number to an index that gauges a risk of subsequent gastrointestinal impairment-based on the predefined spectral events.

14. The system of claim 13, wherein the predefined parameters include frequency of the predefined spectral events and the frequency is in the range of approximately 900 to 20,000 Hertz.

15. The system of claim 13, wherein the predefined parameters include duration of the predefined spectral events and the duration is in the range of approximately 5 to 600 milliseconds.

16. The system of claim 13, wherein the predefined parameters include minimum separation in time of the predefined spectral events from other spectral events and the minimum separation in time is approximately 20 milliseconds.

17. The system of claim 13, wherein the predefined parameters include signal-to-noise ratio of the predefined spectral events and the signal-to-noise ratio threshold is approximately 10 decibels.

18. The system of claim 13, wherein the data collection device docks with the patient monitoring system.

19. The system of claim 13, wherein the single microphone is a laser microphone.

* * * * *